(12) United States Patent
Jansson et al.

(10) Patent No.: US 11,110,213 B2
(45) Date of Patent: Sep. 7, 2021

(54) MIXING FOR ONLINE MEDICAL FLUID GENERATION

(71) Applicants: Baxter International Inc., Deerfield, IL (US); Baxter Healthcare S.A., Glattpark (CH)

(72) Inventors: Olof Jansson, Vellinge (SE); Anders J. Wellings, Belleair Beach, FL (US)

(73) Assignee: Gambro Lundia AB, Lund (SE)

( * ) Notice: Subject to any disclaimer, the term of this patent is extended or adjusted under 35 U.S.C. 154(b) by 207 days.

(21) Appl. No.: 16/175,355

(22) Filed: Oct. 30, 2018

(65) Prior Publication Data
US 2019/0125952 A1 May 2, 2019

Related U.S. Application Data

(60) Provisional application No. 62/580,228, filed on Nov. 1, 2017.

(51) Int. Cl.
*A61M 1/14* (2006.01)
*A61M 1/16* (2006.01)
(Continued)

(52) U.S. Cl.
CPC ........ *A61M 1/1656* (2013.01); *A61M 1/1621* (2014.02); *A61M 1/1668* (2014.02);
(Continued)

(58) Field of Classification Search
CPC .............. A61M 1/1621; A61M 1/1656; A61M 1/1668; A61M 1/1694; A61M 1/28;
(Continued)

(56) References Cited

U.S. PATENT DOCUMENTS 4,388,184 A * 6/1983 Brous ................. A61M 1/1656
210/101
5,616,305 A * 4/1997 Mathieu ............ B01F 15/00824
422/261

(Continued)

FOREIGN PATENT DOCUMENTS

| EP | 2670373 B1 | 2/2012 |
| EP | 3238755 A1 | 11/2017 |
| WO | 2016104761 A1 | 6/2016 |

OTHER PUBLICATIONS

International Preliminary Report on Patentability for related International Application No. PCT/US2018/058192; action dated Feb. 14, 2020; (27 pages).
International Search Report and Written Opinion dated Feb. 13, 2019 in corresponding PCT Application No. PCT/US2018/058192; 15 Pages.

*Primary Examiner* — Pranav N Patel
(74) *Attorney, Agent, or Firm* — K&L Gates LLP

(57) ABSTRACT

A dialysis system includes: (i) a source of water made suitable for a dialysis treatment; (ii) at least one concentrate for mixing with the water from the source; (iii) a dialysis fluid pump; and (iv) a disposable set operable with the dialysis fluid pump and in fluid communication with the source of water and the at least one concentrate, the disposable set including a container having a first end and a second end, the container configured to allow the water and the at least one concentrate pumped by the dialysis fluid pump to enter at the second end and exit from the first end to mix for the dialysis treatment.

28 Claims, 5 Drawing Sheets

(51) Int. Cl.
  *A61M 1/28* (2006.01)
  *A61M 1/36* (2006.01)
  *B01D 61/24* (2006.01)

(52) U.S. Cl.
  CPC ............ *A61M 1/1694* (2013.01); *A61M 1/28* (2013.01); *A61M 1/287* (2013.01); *A61M 1/3635* (2014.02); *A61M 2205/12* (2013.01); *A61M 2205/123* (2013.01); *A61M 2205/3334* (2013.01); *B01D 61/243* (2013.01)

(58) Field of Classification Search
  CPC ................ A61M 1/287; A61M 1/3635; A61M 2205/12; A61M 2205/123; A61M 2205/3334; B01D 61/243; H04B 1/7163; H04B 1/71637; H04B 1/7183; A61J 1/20; A61J 1/10; A61J 1/2058; A61J 1/2062
  See application file for complete search history.

(56) References Cited

U.S. PATENT DOCUMENTS

| | | | |
|---|---|---|---|
| 2002/0103453 A1* | 8/2002 | Burbank | A61M 1/342 604/4.01 |
| 2010/0069817 A1* | 3/2010 | Falkvall | A61M 1/1656 604/6.11 |
| 2012/0288572 A1* | 11/2012 | Kugelmann | A61P 13/12 424/678 |
| 2013/0333795 A1 | 12/2013 | Balschat et al. | |
| 2014/0018727 A1* | 1/2014 | Burbank | A61M 1/288 604/28 |
| 2014/0175126 A1* | 6/2014 | Carlsson | A61M 1/1666 222/145.5 |
| 2015/0029817 A1 | 1/2015 | Orszullok | |
| 2016/0263306 A1* | 9/2016 | Kelly | A61M 1/365 |
| 2017/0043078 A1 | 2/2017 | Thiebaud et al. | |

* cited by examiner

MIXING FOR ONLINE MEDICAL FLUID GENERATION

RELATED APPLICATIONS

This application claims the benefit of and priority to U.S. Provisional Patent Application No. 62/580,228 filed Nov. 1, 2017, entitled "MIXING FOR ONLINE MEDICAL FLUID GENERATION," which is incorporated herein by reference in its entirety.

BACKGROUND

The present disclosure relates generally to medical fluid devices. More specifically, the present disclosure relates to medical fluid devices that mix fluid online for treatment or that receive fluid mixed online for treatment.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products than a patient receiving less frequent but perhaps longer treatments. A patient receiving more frequent treatments does not experience as much of a down cycle as does an in-center patient, who has built-up two or three day's worth of toxins prior to a treatment. In certain areas, the closest dialysis center can be many miles from the patient's home, causing door-to-door treatment time to consume a large portion of the day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" may occur at the end of the APD treatment. The fluid may remain in the peritoneal cavity of the patient until the start of the next treatment, or may be manually emptied at some point during the day.

In any of the above modalities using an automated machine, treatment fluid may be prepared online or at the point of use, e.g., before and/or during the treatment. It is important that the treatment fluid, e.g., dialysis fluid be mixed properly and homogeneously for treatment. A need exists for improved mixing accordingly.

SUMMARY

The examples described herein disclose automated systems and methods applicable, for example, to fluid delivery for: peritoneal dialysis ("PD"), plasmapherisis, hemodialysis ("HD"), hemofiltration ("HF") hemodiafiltration ("HDF"), continuous renal replacement therapy ("CRRT"), apheresis, autotransfusion, hemofiltration for sepsis, and extracorporeal membrane oxygenation ("ECMO") treatments. The systems and methods described herein are applicable to any medical fluid delivery system in which the treatment fluid may be made online or at the point of use, e.g., just before and/or during treatment. These modalities may be referred to collectively or generally individually herein as medical fluid delivery system(s).

Moreover, each of the systems and methods described herein may be used with clinical or home-based treatments. For example, the present systems and methods may be employed in in-center PD, HD, HF or HDF machines, which run throughout the day. Alternatively, the present systems and methods may be used with home PD, HD, HF or HDF machines, which are operated generally at the patient's convenience.

In one embodiment, a peritoneal dialysis system and method is provided having point of use dialysis fluid production. The system includes a cycler and a water purifier. The cycler includes a control unit having at least one processor and at least one memory. The cycler may further include a wired or wireless transceiver for sending information to and receiving information from the water purifier. The water purifier may also include a control unit having at least one processor and at least one memory and a wired or wireless transceiver for sending information to and receiving information from the control unit of the cycler.

The cycler includes equipment programmed via its control unit to prepare fresh dialysis solution at the point of use, pump the freshly prepared dialysis fluid to a patient, allow the dialysis fluid to dwell within the patient, then pump used dialysis fluid to a drain. The cycler in one embodiment includes a heater under control of the control unit for heating the dialysis fluid as it is being mixed in one embodiment. The heater may for example be located at the top of a housing of the cycler, e.g., beneath a heating lid.

The cycler (and the water purifier in one embodiment) operates with a disposable set. The disposable set in one embodiment includes a disposable cassette, which may include a planar rigid plastic piece covered on one or both sides by a flexible membrane, forming fluid pumping and valving chambers. The fluid pump chambers may operate with pneumatic pump chambers of the cycler, while fluid valve chambers operate with the pneumatic valve chambers of the cycler.

The disposable set may include (i) a patient line that extends from the cassette to a patient line connector, (ii) a drain line that extends from the cassette to a drain line connector (which may in turn connect removeably to the water purifier), (iii) a heater/mixing line that extends from the cassette to a heater/mixing bag of the present disclosure, (iv) an upstream water line segment that extends from the water purifier to a water inlet of a water accumulator and a downstream water line segment that extends from a water outlet of the water accumulator to the cassette, (v) a last bag or sample line that extends from the cassette to a premixed last fill bag of dialysis fluid or to a sample bag or other sample collecting container, (vi) a first, e.g., glucose, concentrate line extending from the cassette to a first, e.g., glucose, concentrate container, and/or (vii) a second, e.g., buffer, concentrate line that extends from the cassette to a second, e.g., buffer, concentrate container.

The heater/mixing container or bag of the present disclosure may be provided in a plurality of different configurations that ensure that at least one concentrate (e.g., glucose and buffer) and water made suitable for treatment, e.g., water made suitable for peritoneal dialysis ("WFPD"), are delivered into the container at one end, e.g., the distal end, of the container while the at least one concentrate and WFPD further mixed for treatment are removed from the container at an opposing, e.g., the proximal end of the container. In one embodiment the proximal end of the container is a first end, while the distal end of the container is a second end. In one embodiment, the at least one concentrate and WFPD are already at least partially mixed before entering the container. In another embodiment, the WFPD and the at least one concentrate are delivered separately to the container and mix for the first time in a tube or passageway located within the container or bag.

In one primary embodiment, the container includes a first, proximal end, a second, distal end, and a pair of opposing sides extending between the first and second ends. The container may be square or rectangular or have one or more curved end or surface. The container may be a flexible bag made of any of the materials disclosed herein. A connector is placed in sealed communication with the first end of the container. For example, sheeting of the first end of a flexible bag may be heat sealed, sonically or ultrasonically sealed, solvent bonded and/or adhered to the connector, which may be a rigid or semi-rigid plastic made of any of the materials disclosed herein. The connector in one embodiment may include a inlet and outlet legs that Y or T together outside of the container or bag, so as to form a single heater/mixing line extending to the cassette. The legs of the Y or T connector may be formed integrally with the single heater/mixing line extending to the cassette, be connected via a luer connection to the single heater/mixing line, or be connected via a compression fitting, e.g., barbed fitting with the single heater/mixing line.

The legs of the Y or T connector are each fitted in one embodiment with a one way valve, e.g., a duckbilled check valve, positioned so that the WFPD and at least one concentrate cannot (i) enter through an outlet one of the legs of the Y or T connector or (ii) exit through an inlet one of the legs of the Y or T connector. The inlet leg of the Y or T connector extends as a tube into the interior of the container or bag and all the way from the first end to the second end of the container or bag, so that the WFPD and at least one concentrate are forced to enter the interior of the container or bag at the second or distal end. The outlet leg of the Y or T connector extends as a short tube or port just inside the interior of the container or bag at the first end, so that the WFPD and at least one concentrate are forced to exit the interior of the container or bag at the first or proximal end. In this manner, the WFPD and at least one concentrate are forced to traverse the entire length of the container or bag from the second end to the first end before leaving the container or bag, thereby increasing time and turbidity for mixing, prior to exiting the container or bag and returning to the pumping and valving cassette.

In an embodiment, the connector is located along the first end of the container or bag adjacent to a corner of the bag formed by the first end and one of the first or second sides, and wherein the inlet leg tube is caused to extend to an opposite corner formed by the second end and the other of the first or second sides of the container. In this manner the diagonal length of travel of the WFPD and at least one concentrate from the second end to the first end before leaving the container or bag is maximized. In an alternative embodiment, an outlet leg tube is provided along with the inlet leg tube, and wherein at least one of the inlet leg tube and the outlet leg tube is capped at its distal or second end and provided instead with multiple small holes along the length the tube—can leave or take out, helps versus design-arounds.

In a second primary embodiment, the container may again include a first, proximal end, a second, distal end and a pair of opposing sides extending between the first and second ends. The container may be square or rectangular or have one or more curved end or surface. The container may be a flexible bag made of any of the materials disclosed herein. A connector is placed in sealed communication with the first end of the container. For example, sheeting of the first end of a flexible bag may be heat sealed, sonically or ultrasonically sealed, solvent bonded and/or adhered to the connector, which may be a rigid or semi-rigid plastic made of any of the materials disclosed herein. The connector in the second primary embodiment does not Y or T together outside of the container or bag, and instead includes a single port sealed to the heater/mixing line extending to the cassette. The single port may be connected via a luer connection to the single heater/mixing line, or be connected via a compression fitting, e.g., a barbed fitting, with the single heater/mixing line.

The connector of the second primary embodiment may include a tapered body, wherein the body has a thickness that enables multiple grooves to be formed on the upper and lower surfaces of the tapered body. The body also defines an inlet aperture for allowing the WFPD and at least one concentrate to enter the container from the cassette and an outlet aperture for allowing mixed or further mixed WFPD and at least one concentrate to exit the container towards the cassette. In one embodiment, the inlet aperture of the connector is placed in fluid communication with an inlet passageway defined by the container itself, e.g., a passageway formed via seals made between two flexible sheets forming the bag or container. The inlet passageway, like the inlet leg tube of the first primary embodiment, may extend to the second or distal end of the container, e.g., to a corner of the second or distal end of the container located diagonally opposite from a corner at the first or proximal end of the container at which the connector is located. The connector may alternatively be located at an approximate middle of the first or proximal end of the container. In either case, the WFPD and at least one concentrate are introduced into the interior of the container at its second or distal end.

The outlet aperture of the connector is in one embodiment placed in fluid communication with the plurality of grooves formed along the upper and lower surfaces of the connector. The connector is sealed to the remainder of the container, e.g., flexible sheets, such that the further mixed WFPD and at least one concentrate can enter the grooves from at least one entry location and flow through the grooves to the outlet aperture, and from the outlet aperture out of the container and through the heater/mixing line to the cassette.

In one embodiment, a one way valve, such as a duckbilled check valve, is placed into, or adjacent to, the outlet aperture so that when the heater/mixing line is placed under positive pressure to drive the WFPD and at least one concentrate into the container, the WFPD and at least one concentrate are prevented from flowing from the inside of the container, through the grooves of the connector and out of the connector into the heater/mixing line. It is believed that a second one way valve is not needed for the inlet aperture of the connector because when the heater/mixing line is placed under negative pressure to pull the WFPD and at least one concentrate from the container, the flexible passageway, made by sealing the bag sheeting in one embodiment to create seams defining the passageway, will collapse under the negative pressure causing the inlet passageway to close itself, preventing the WFPD and at least one concentrate from being pulled out of the container from the inlet passageway before the WFPD and at least one concentrate have a chance to mix in the container.

Both of the above primary embodiments aid in mixing WFPD and at least one concentrate. In an embodiment, the medical fluid delivery system, e.g., a peritoneal dialysis system, is programmed to perform a mixing sequence in which the machine or cycler pumps the WFPD and at least one concentrate fluid from the cassette, to the heater/mixing container or bag, and back to the cassette and repeats this sequence multiple times. Each time the sequence is repeated, the mixing of the WFPD and at least one concentrate is aided by being introduced at one end of the container and removed at the other end of the container, wherein it is ensured that the WFPD and concentrate have to travel the length of the container, increasing contact time and surface area exchange.

In light of the disclosure herein and without limiting the disclosure in any way, in a first aspect of the present disclosure, which may be combined with any other aspect listed herein unless specified otherwise, a dialysis system includes: a source of water made suitable for a dialysis treatment; at least one concentrate for mixing with the water from the source; a dialysis fluid pump; and a disposable set operable with the dialysis fluid pump and in fluid communication with the source of water and the at least one concentrate, the disposable set including a container having a first end and a second end, the container configured to allow the water and the at least one concentrate pumped by the dialysis fluid pump to enter at the second end and exit from the first end to mix for the dialysis treatment.

In a second aspect of the present disclosure, which may be combined with any other aspect listed herein unless specified otherwise, the dialysis system is configured such that the water and the at least one concentrate pumped by the dialysis fluid pump enter the container partially mixed together.

In a third aspect of the present disclosure, which may be combined with any other aspect listed herein unless specified otherwise, the container is a flexible bag.

In a fourth aspect of the present disclosure, which may be combined with any other aspect listed herein unless specified otherwise, the disposable set includes a pumping cassette that interfaces with the dialysis fluid pump.

In a fifth aspect of the present disclosure, which may be combined with the fourth aspect in combination with any other aspect listed herein unless specified otherwise, the water and the at least one concentrate are mixed initially in the pumping cassette.

In a sixth aspect of the present disclosure, which may be combined with the fourth aspect in combination with any other aspect listed herein unless specified otherwise, the dialysis fluid pump pneumatically actuates the pumping cassette.

In a seventh aspect of the present disclosure, which may be combined with the fourth aspect in combination with any other aspect listed herein unless specified otherwise, the disposable set system includes a tube extending from the pumping cassette to the container.

In an eighth aspect of the present disclosure, which may be combined with the seventh aspect in combination with any other aspect listed herein unless specified otherwise, the tube is a first tube and wherein the disposable set includes at least one second tube extending from the pumping cassette to the at least one concentrate.

In a ninth aspect of the present disclosure, which may be combined with the seventh aspect in combination with any other aspect listed herein unless specified otherwise, the tube is a first tube and wherein the disposable set includes a second tube extending from the pumping cassette to an accumulator that receives the water made suitable for the dialysis treatment from the source.

In a tenth aspect of the present disclosure, which may be combined with the fourth aspect in combination with any other aspect listed herein unless specified otherwise, the system is configured to pump the water and the at least one concentrate back and forth from the pumping cassette to the container a plurality of times to perform a mixing sequence for further mixing.

In an eleventh aspect of the present disclosure, which may be combined with any other aspect listed herein unless specified otherwise, the container includes a connector having a port at the first end of the container and a tube extending within container from the port to the second end of the container.

In a twelfth aspect of the present disclosure, which may be combined with the eleventh aspect in combination with any other aspect listed herein unless specified otherwise, wherein at least one of the port and the tube are in fluid communication with a one way valve.

In a thirteenth aspect of the present disclosure, which may be combined with the eleventh aspect in combination with any other aspect listed herein unless specified otherwise, the system is configured to deliver the water and the at least one concentrate into the container via the tube at the second end and remove the further mixed water and at least one concentrate from the container via the port connector at the first end.

In a fourteenth aspect of the present disclosure, which may be combined with any other aspect listed herein unless specified otherwise, the container is sealed so as to form a passageway leading to the second end of the container.

In a fifteenth aspect of the present disclosure, which may be combined with the fourteenth aspect in combination with any other aspect listed herein unless specified otherwise, the first end includes a connector, the connector defining at least one groove positioned and arranged to allow further mixed water and at least one concentrate to travel through the at least one groove to a port of the container.

In a sixteenth aspect of the present disclosure, which may be combined with the fifteenth aspect in combination with any other aspect listed herein unless specified otherwise, the port is formed as part of the connector.

In a seventeenth aspect of the present disclosure, which may be combined with the fifteenth aspect in combination with any other aspect listed herein unless specified otherwise, the passageway extends from and fluidly communicates with an aperture defined by the connector.

In an eighteenth aspect of the present disclosure, which may be combined with the seventeenth aspect in combination with any other aspect listed herein unless specified otherwise, the aperture is a first aperture and which includes a second aperture defined by the connector allowing the water and the at least one concentrate at least partially mixed for the dialysis treatment to exit the container.

In a nineteenth aspect of the present disclosure, which may be combined with the eighteenth aspect in combination with any other aspect listed herein unless specified otherwise, the second aperture is fitted with or located adjacent to a one way valve.

In a twentieth aspect of the present disclosure, which may be combined with the fourteenth aspect in combination with any other aspect listed herein unless specified otherwise, the passageway is structured to collapse under negative pressure.

In a twenty-first aspect of the present disclosure, which may be combined with any other aspect listed herein unless specified otherwise, a dialysis system includes: a source of water made suitable for a dialysis treatment; at least one concentrate for mixing with the water from the source; and a disposable set in fluid communication with the source of water and the at least one concentrate, the disposable set including a container having a first end and a second end, the container including (i) a tube structured and arranged to allow the water and the at least one concentrate to enter the container at the second end and (ii) a port at the first end for the water and the at least one concentrate at least partially mixed for the dialysis treatment to exit the container.

In a twenty-second aspect of the present disclosure, which may be combined with the twenty-first aspect in combination with any other aspect listed herein unless specified otherwise, the tube and the port connect at a junction outside of the container.

In a twenty-third aspect of the present disclosure, which may be combined with the twenty-first aspect in combination with any other aspect listed herein unless specified otherwise, at least one of the tube and the port is fitted with a one way valve.

In a twenty-fourth aspect of the present disclosure, which may be combined with any other aspect listed herein unless specified otherwise, a dialysis system includes: a source of water made suitable for a dialysis treatment; at least one concentrate for mixing with the water from the source; and a disposable set in fluid communication with the source of water and the at least one concentrate, the disposable set including a container having a first end and a second end, the container sealed so as to form a passageway leading to the second end of the container, wherein the water and the at least one concentrate flow through the passageway to enter the container at the second end, the container further including a port at the first end for the water and the at least one concentrate at least partially mixed for the dialysis treatment to exit the container.

In a twenty-fifth aspect of the present disclosure, which may be combined with the twenty-fourth aspect in combination with any other aspect listed herein unless specified otherwise, the first end of the container includes a connector, the connector defining at least one groove positioned and arranged to allow the water and the at least one concentrate at least partially mixed for the dialysis treatment to travel through the at least one groove to the port to exit the container.

In a twenty-sixth aspect of the present disclosure, which may be combined with the twenty-fifth aspect in combination with any other aspect listed herein unless specified otherwise, the port is formed as part of the connector.

In a twenty-seventh aspect of the present disclosure, which may be combined with the twenty-fifth aspect in combination with any other aspect listed herein unless specified otherwise, the passageway extends from and fluidly communicates with an aperture defined by the connector.

In a twenty-eighth aspect of the present disclosure, which may be combined with the twenty-seventh aspect in combination with any other aspect listed herein unless specified otherwise, the aperture is a first aperture and which includes a second aperture defined by the connector, the second aperture allowing the water and the at least one concentrate at least partially mixed for the dialysis treatment to exit the container.

In a twenty-ninth aspect of the present disclosure, which may be combined with the twenty-eighth aspect in combination with any other aspect listed herein unless specified otherwise, the second aperture is fitted with or adjacent to a one way valve.

In a thirtieth aspect of the present disclosure, which may be combined with the twenty-fourth aspect in combination with any other aspect listed herein unless specified otherwise, the passageway is structured to collapse under negative pressure.

In a thirty-first aspect of the present disclosure, any of the structure, functionality and alternatives disclosed in connection with FIGS. 1 to 5B may be combined with any of the other structure, functionality and alternatives disclosed in connection with FIGS. 1 to 5B.

In light of the present disclosure and the above aspects, it is therefore an advantage of the present disclosure to provide an improved medical fluid delivery system.

It is another advantage of the present disclosure to provide an improved medical fluid delivery system that prepares treatment fluid online or at the point of use.

It is a further advantage of the present disclosure to provide an improved mixing structure and methodology for a medical fluid delivery system that prepares treatment fluid online or at the point of use.

The advantages discussed herein may be found in one, or some, and perhaps not all of the embodiments disclosed herein. Additional features and advantages are described herein, and will be apparent from, the following Detailed Description and the figures.

DETAILED DESCRIPTION

System Overview

The examples described herein are applicable to any medical fluid therapy system that delivers a medical fluid that may be mixed at the point of use, prior to and/or during treatment, such as dialysis fluid, substitution fluid, or an intravenous drug. The examples are particularly well suited for kidney failure therapies, such as all forms of peritoneal dialysis ("PD"), hemodialysis ("HD"), hemofiltration ("HF"), hemodiafiltration ("HDF") and continuous renal replacement therapies ("CRRT"), referred to herein collectively or generally individually as renal failure therapy. Moreover, the machines described herein may be used in clinical or home settings. For example, the machines and associated methods may be employed in an in-center PD or HD machine, which runs virtually continuously throughout the day. Alternatively, the machine and methods may be used in a home PD or HD machine, which can for example be run at night while the patient is sleeping. The machines and methods discussed herein are also applicable to medical delivery applications. The following examples will be described in the setting of a peritoneal dialysis system having point of use dialysis fluid production but may instead be used to make point of use treatment fluid for any of the above modalities.

Figure 1:
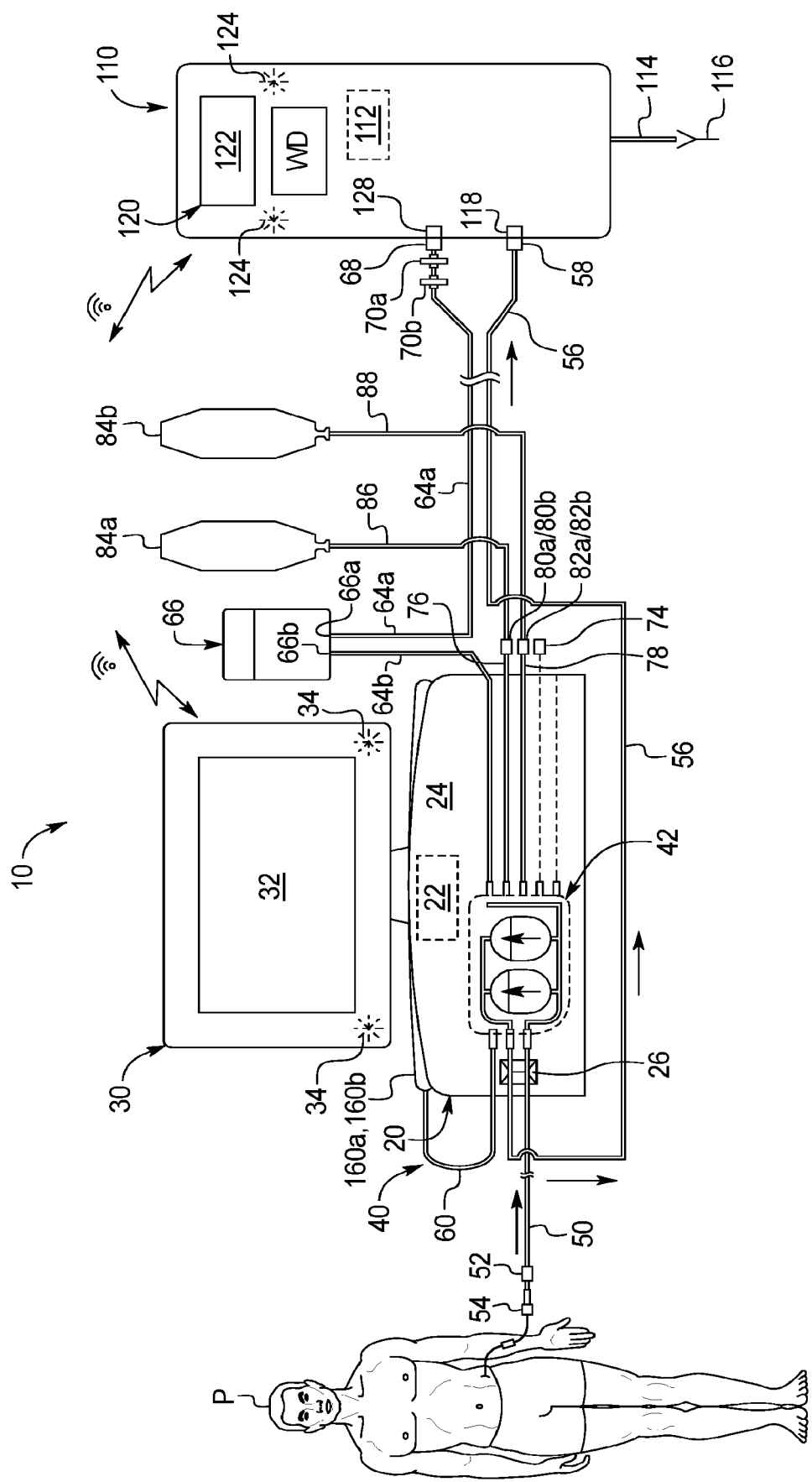
FIG. 1 is a front elevation view of one embodiment of a medical fluid delivery system having point of use dialysis fluid production of the present disclosure.

Referring now to the drawings and in particular to FIG. 1, one embodiment of a peritoneal dialysis system having point of use dialysis fluid production of the present disclosure is illustrated by system 10. System 10 includes a cycler 20 and a water purifier 110. Suitable cyclers for cycler 20 include, e.g., the Amia® or HomeChoice® cycler marketed by Baxter International Inc., with the understanding that those cyclers are provided with updated programming to perform and use the point of use dialysis fluid produced according to system 10. To this end, cycler 20 includes a control unit 22 having at least one processor and at least one memory. Control unit 22 further includes a wired or wireless transceiver for sending information to and receiving information from a water purifier 110. Water purifier 110 also includes a control unit 112 having at least one processor and at least one memory. Control unit 112 further includes a wired or wireless transceiver for sending information to and receiving information from control unit 22 of cycler 20. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purifier includes a drain line 114 leading to a drain 116, which can be a house drain or a drain container. The equipment programmed via control unit 22 to prepare fresh dialysis solution at the point of use in an embodiment includes equipment for a pneumatic pumping system, including but not limited to (i) one or more positive pressure reservoir, (ii) one or more negative pressure reservoir, (iii) a compressor and a vacuum pump each under control of control unit 22, or a single pump creating both positive and negative pressure under control of control unit 22, to provide positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off pneumatic solenoid valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (ix) an occluder 26 under control of control unit 22 for closing the patient and drain lines in alarm and other situations.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan, which is located at the top of housing 24, beneath a heating lid (not seen in FIG. 1).

Cycler 20 in the illustrated embodiment includes a user interface 30. Control unit 22 in an embodiment includes a video controller, which may have its own processing and memory for interacting with primary control processing and memory of control unit 22. User interface 30 includes a video monitor 32, which may operate with a touch screen overlay placed onto video monitor 32 for inputting commands via user interface 30 into control unit 22. User interface 30 may also include one or more electromechanical input device, such as a membrane switch or other button. Control unit 22 may further include an audio controller for playing sound files, such as voice activation commands, at one or more speaker 34.

Water purifier 110 in the illustrated embodiment also includes a user interface 120. Control unit 112 of water purifier 110 in an embodiment includes a video controller, which may have its own processing and memory for interacting with primary control processing and memory of control unit 112. User interface 120 includes a video monitor 122, which may likewise operate with a touch screen overlay placed onto video monitor 122 for inputting commands into control unit 112. User interface 120 may also include one or more electromechanical input device, such as a membrane switch or other button. Control unit 112 may further include an audio controller for playing sound files, such as alarm or alert sounds, at one or more speaker 124 of water purifier 110.

Figure 2:
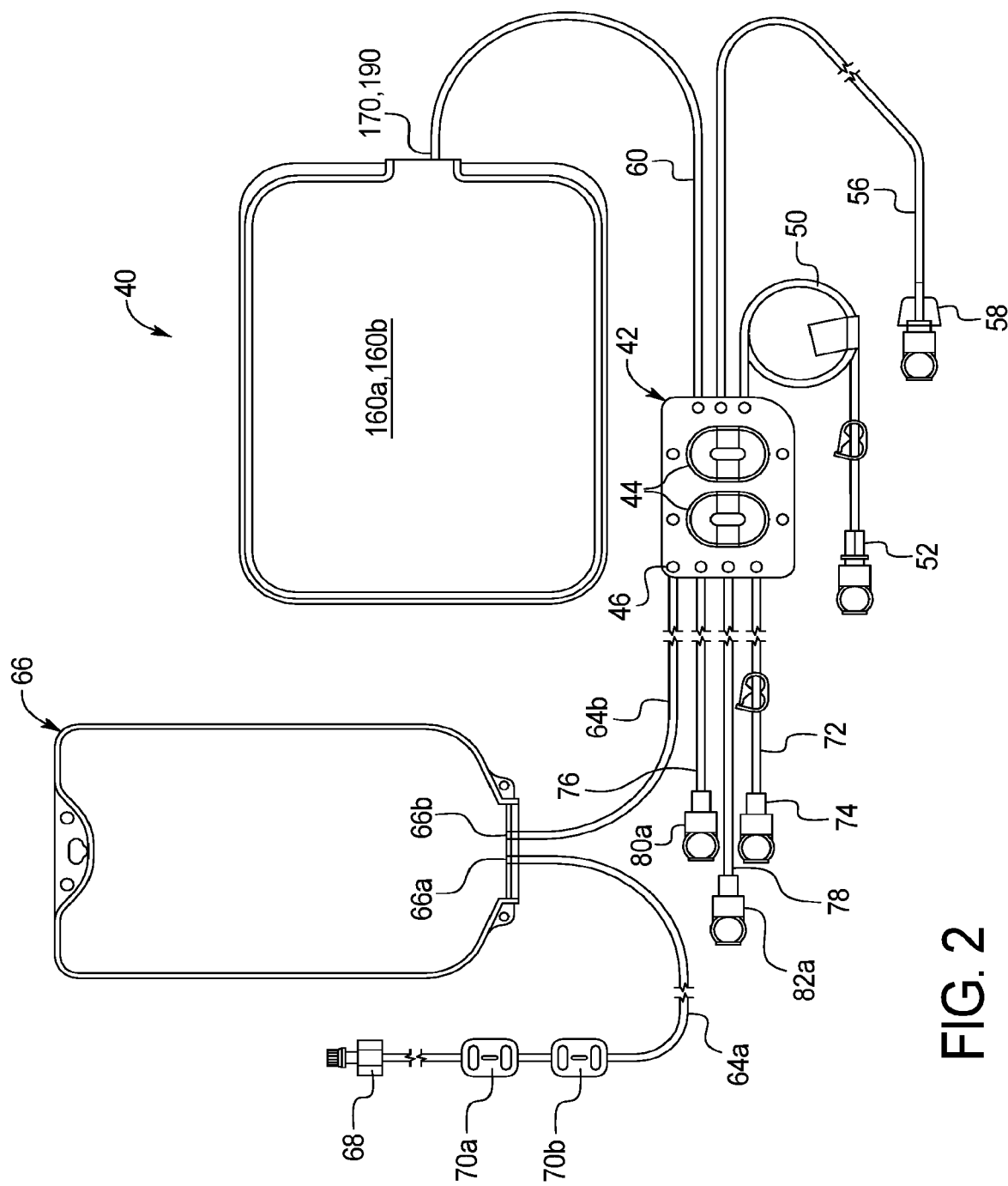
FIG. 2 is an elevation view of one embodiment of a disposable set used with the system illustrated in FIG. 1.

Referring additionally to FIG. 2, one embodiment of disposable set 40 is illustrated. Disposable set 40 is also illustrated in FIG. 1, mated to cycler 20 to move fluid within the disposable set 40, e.g., to mix dialysis fluid as discussed herein. Disposable set 40 in the illustrated embodiment includes a disposable cassette 42, which may include a planar rigid plastic piece covered on one or both sides by a flexible membrane. The membrane pressed against housing 24 of cycler 20 forms a pumping and valving membrane. FIG. 2 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20.

FIGS. 1 and 2 illustrate that disposable set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P. Disposable set 40 includes a drain line 56 that extends from a drain line port of cassette 42 and terminates at a drain line connector 58. FIG. 1 illustrates that drain line connector 58 connects removeably to a drain connector 118 of water purifier 110.

FIGS. 1 and 2 further illustrate that disposable set 40 includes a heater/mixing line 60 that extends from a heater/mixing line port of cassette 42 and terminates at a heater/mixing bag 160a, 160b discussed in more detail below. Disposable set 40 includes an upstream water line segment 64a that extends to a water inlet 66a of water accumulator 66. A downstream water line segment 64b extends from a water outlet 66b of water accumulator 66 to cassette 42. In the illustrated embodiment, upstream water line segment 64a begins at a water line connector 68 and is located upstream from water accumulator 66. FIG. 1 illustrates that water line connector 68 is removeably connected to a water outlet connector 128 of water purifier 110.

Water purifier 110 outputs water and possibly water suitable for peritoneal dialysis ("WFPD"). To ensure WFPD, however, a sterile sterilizing grade filter 70a is placed upstream from a downstream sterile sterilizing grade filter 70b, respectively. Filters 70a and 70b may be placed in water line segment 64a upstream of water accumulator 66. Sterile sterilizing grade filters 70a and 70b may be pass-through filters that do not have a reject line. Pore sizes for filters 70a and 70b may, for example, be less than a micron, such as 0.1 or 0.2 micron. Suitable sterile sterilizing grade filters 70a and 70b may be provided by the assignee of the present disclosure. In an embodiment, only one of upstream or downstream sterilizing filter 70a and 70b is needed to produce WFPD, nevertheless, two sterile sterilizing grade filters 70a and 70b are provided in the illustrated embodiment for redundancy in case one fails.

FIG. 2 further illustrates that a last bag or sample line 72 may be provided that extends from a last bag or sample port of cassette 42. Last bag or sample line 72 terminates at a connector 74, which may be connected to a mating connector of a premixed last fill bag of dialysis fluid or to a sample bag or other sample collecting container. Last bag or sample line 72 and connector 74 may be used alternatively for a third type of concentrate if desired.

FIGS. 1 and 2 illustrate that disposable set 40 includes a first, e.g., glucose, concentrate line 76 extending from a first concentrate port of cassette 42 and terminates at a first, e.g., glucose, cassette concentrate connector 80a. A second, e.g., buffer, concentrate line 78 extends from a second concentrate port of cassette 42 and terminates at a second, e.g., buffer, cassette concentrate connector 82a.

FIG. 1 illustrates that a first concentrate container 84a holds a first, e.g., glucose, concentrate, which is pumped from container 84a through a container line 86 to a first container concentrate connector 80b, which mates with first cassette concentrate connector 80a. A second concentrate container 84b holds a second, e.g., buffer, concentrate, which is pumped from container 84b through a container line 88 to a second container concentrate connector 82b, which mates with second cassette concentrate connector 82a.

In an embodiment, to begin treatment, patient P loads cassette 42 into cycler and in a random or designated order (i) places heater/mixing bag 160a, 160b onto cycler 20, (ii) connects upstream water line segment 64a to water outlet connector 128 of water purifier 110, (iii) connects drain line 56 to drain connector 118 of water purifier 110, (iv) connects first cassette concentrate connector 80a to first container concentrate connector 80b, and (v) connects second cassette concentrate connector 82a to second container concentrate connector 82b. At this point, patient connector 52 is still capped. Once fresh dialysis fluid is prepared and verified, patient line 50 is primed with fresh dialysis fluid, after which patient P may connect patient line connector 52 to transfer set 54 for treatment. Each of the above steps may be illustrated graphically at video monitor 32 and/or be provided via voice guidance from speakers 34.

For disposable set 40, the rigid portion of cassette 42 may be made for example of a thermal olefin polymer of amorphous structure ("TOPAS") cyclic olefin copolymer ("coc"). The flexible membranes of cassette 42 may be made for example of a copolyletser ether ("PCCE") and may be of one or more layer. Any of the tubing or lines may be made for example of polyvinyl chloride ("PVC"). Any of the connectors may be made for example of acrylonitrile-butadienestyrene ("ABS", e.g., for connectors 170 and 190 of heater/mixing bags or containers 160a and 160b, respectively, discussed below, for concentrate connectors 80a, 80b, 82a, 82b and heater/mixing bag connector 170, 190 discussed below), acrylic (e.g., for drain line connector 58) or PVC (e.g., for water line connector water line connector 68). Any of the bags or containers, such as bags or containers 160a and 160b discussed below, may be made of PVC. The materials for any of the above components may be changed over time.

Mixing/Heater Bag

Control unit 22 may be programmed to cause cycler 20 to perform one or more mixing action to help mix dialysis fluid properly and homogeneously for treatment. For example, any of fluid pump chambers 44 may be caused to withdraw into the pump chambers some amount of mixed fluid (e.g., made from one or both first and second concentrates 84a, 84b and WFPD) from heater/mixing bag 160a, 160b, to send such mixture back to heater/mixing bag 160a, 160b, and repeat this procedure multiple times (described herein as a mixing sequence or "waffling"). In particular, to perform a mixing sequence, control unit 22 in an embodiment causes cycler 20 to close all fluid valve chambers 46 at cassette 42 except for the fluid valve chamber 46 to heater/mixing line 60 and heater/mixing bag 160a, 160b. Fluid pump chambers 44 are stroked sequentially and repeatedly (i) pulling a possibly unmixed fluid combination of WFPD and concentrates from heater/mixing bag 160a, 160b into the pump chambers, followed by (ii) pushing the mixed WFPD and concentrates from the pump chambers back to heater/mixing bag 62, and (iii) repeating (i) and (ii) at least one time. Control unit 22 may be programmed to stroke fluid pump chambers 44 together so that they both pull and push at the same time, or alternatingly so that one pump chamber 44 pulls from heater/mixing bag 160a, 160b, while the other pump chamber 44 pushes to heater/mixing bag 160a, 160b, creating turbulence in heater/mixing line 60.

Each time the waffling sequence is repeated, the mixing of the WFPD and at least one concentrate is aided by being introduced at one end of one of the heater/mixing containers or bags 160a or 160b, described below, and removed at the other end of the container or bag 160a, 160b, wherein it is ensured that the WFPD and concentrate have to travel the length of the container or bag, increasing contact time and surface area exchange. Where containers or bags 160a, 160b operate with cassette 42 and heater/mixing line 60, the WFPD from accumulator 66 and concentrates from first and second concentrate containers 84a and 84b are already at least partially mixed before entering the container or bag. Even if cassette 42 is not provided, the WFPD and at least one concentrate will mix partially in heater/mixing line 60 prior to reaching the container or bag. In another embodiment, however, the WFPD and the at least one concentrate may be delivered separately to container or bag 160a, 160b and mixed for the first time in a tube or passageway located within the container or bag.

Figure 3A:
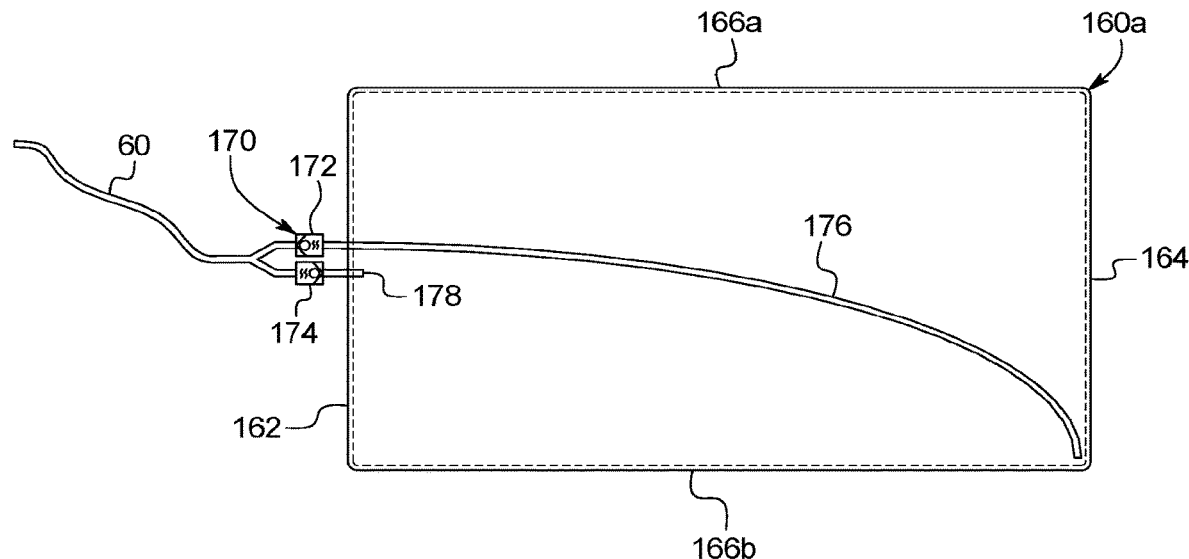
FIGS. 3A and 3B are top, elevation views of alternative versions of a first primary heater/mixing container or bag of the present disclosure.

Referring now to FIG. 3A, to aid the mixing of WFPD and concentrates, heater/mixing container or bag 160a is provided. Container or Bag 160a as illustrated includes a first or proximal end 162, an opposite second or distal end 164 and two sides 166a and 166b extending between ends 162 and 164. Container or bag 160a may be square or rectangular or have one or more curved end or surface. Container 160a may be a flexible bag made of any of the materials disclosed herein. A connector 170 is placed in sealed communication with first or proximal end 162 of the container or bag. In various embodiments, sheeting at a first end 162 of flexible bag 160a may be heat sealed, sonically or ultrasonically sealed, solvent bonded and/or adhered to connector 170, which may be a rigid or semi-rigid plastic, e.g., plastic tubing, made of any of the materials disclosed herein. Connector 170 in one embodiment Y's or T's together outside of the container or bag, so as to form a single heater/mixing line 60 extending to cassette 42. The legs of Y or T connector 170 may be formed integrally with single heater/mixing line 60 extending to the cassette, be connected via a luer connection to single heater/mixing line 60, or be connected via a compression fitting, e.g., barbed fitting, to the single heater/mixing line.

The legs of Y or T connector 170 are each fitted in one embodiment with a one way valve 172 and 174, e.g., a duckbilled check valve, positioned so that the WFPD and at least one concentrate cannot (i) enter through the outlet one of the legs of Y or T connector 170 (stopped by one way valve 174) or (ii) exit through the inlet one of the legs of Y or T connector 170 (stopped by one way valve 172). In particular, one way inlet valve 172 is oriented so as to close when negative pressure is applied to heater/mixing line 60 to remove the further mixed WFPD and at least one concentrate from container 160a, while one way outlet valve 174 remains open to allow for the removal. Conversely, one way outlet valve 174 is oriented so as to close when positive pressure is applied to heater/mixing line 60 to push the WFPD and at least one concentrate into container 160a, while one way inlet valve 172 remains open to allow for the input.

The inlet leg of Y or T connector 170 extends as a tube 176 into the interior of the container or bag 160a and all the way from first or proximal end 162 to the second or distal end 164 of the container or bag, so that the WFPD and at least one concentrate are forced to enter the interior of the container or bag 160a at the second or distal end 164. The outlet leg of Y or T connector 170 extends as a short tube or port 178 just inside the interior of the container or bag 160a at the first end 162, so that the WFPD and at least one concentrate are forced to exit the interior of the container or bag 160a at the first or proximal end 162. In this manner, the WFPD and at least one concentrate are forced to traverse the entire length of container or bag 160a, from second end 164 to first end 162, before leaving the container or bag, thereby increasing time and turbidity for mixing, prior to exiting the container or bag and returning to the pumping and valving cassette 42.

Figure 3B:
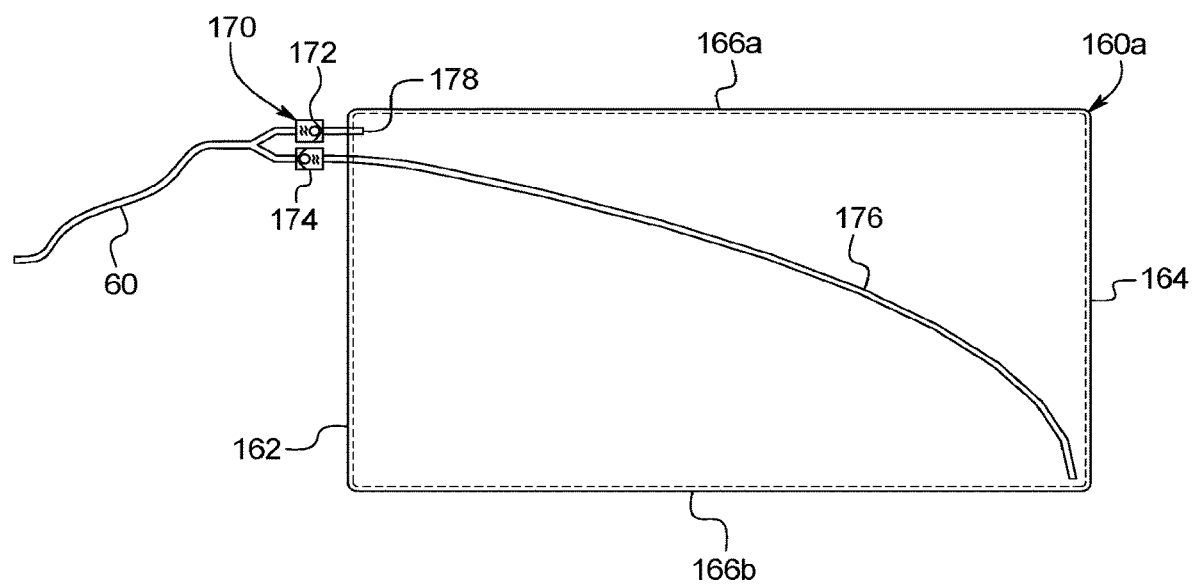

In FIG. 3A, connector 170 is located at an approximate middle of first or proximal end 162. In FIG. 3B, connector 170 is located alternatively along first end 162 of container or bag 160a adjacent a corner of the bag formed by first end 162 and first side 166a. In FIG. 3B, inlet leg tube 176 is sized and/or shaped to extend to an opposite corner formed by second end 164 and second side 166b. In this manner the length of diagonal travel of the WFPD and the at least one concentrate from second end 164 to the first end 162 before leaving container or bag 160a is maximized.

In an alternative embodiment, an outlet leg tube is provided along with the inlet leg tube 176. Here, at least one of the inlet leg tube 176 and the outlet leg tube is capped at its distal or second end and provided instead with multiple small holes or perforations located along the length the tube. The sum of the diameters of the small holes or perforations is at least equal to the inner diameter of inlet leg tube 176 or the outlet leg tube, so as not to create a flow restriction in one embodiment. The diameters of the small holes or perforations may be varied in an attempt to equalize the amount of flow into or out of the holes along the length of the tubes.

Figure 4:
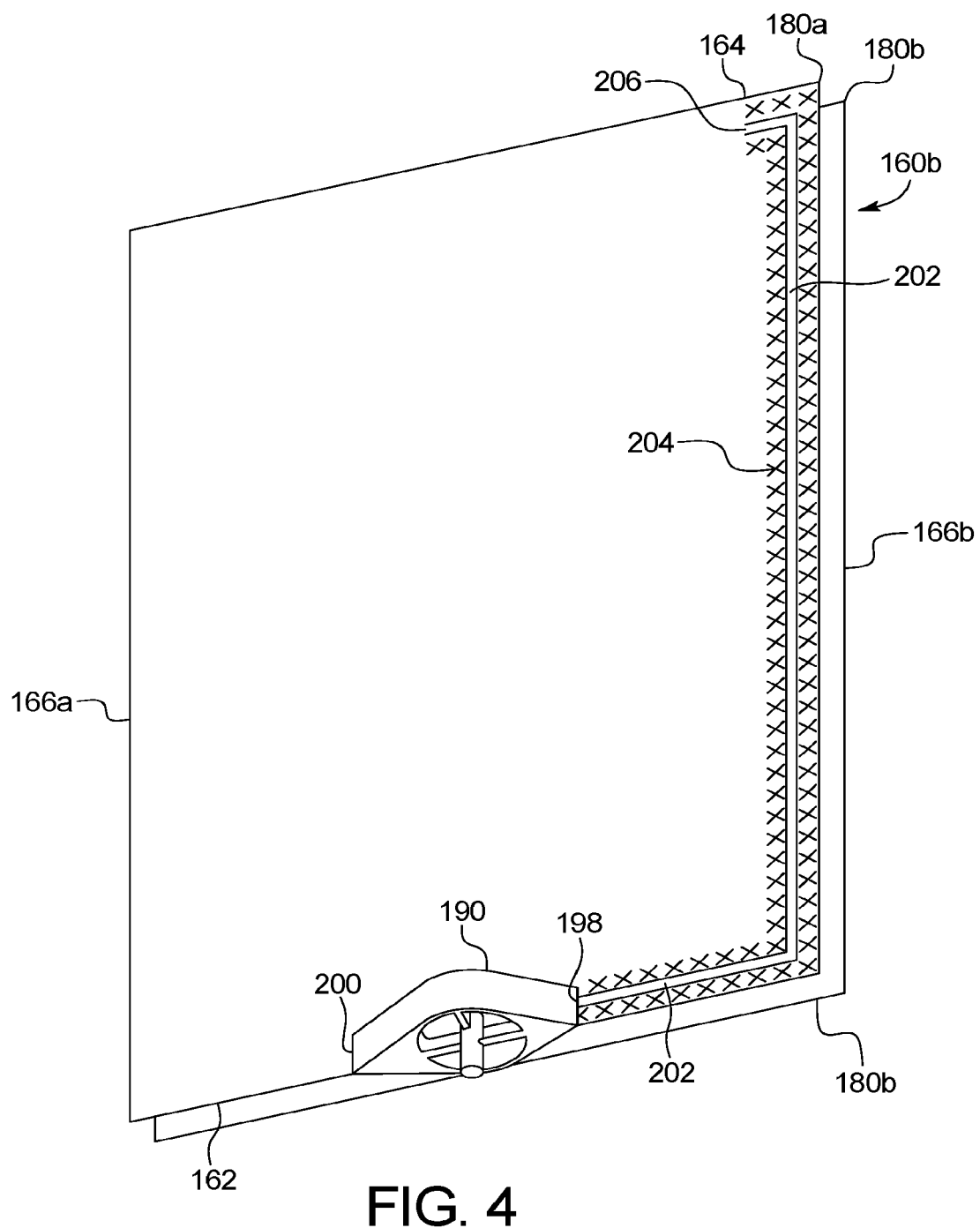
FIG. 4 is a perspective view of one embodiment of a second primary heater/mixing container or bag of the present disclosure.
Figure 5A:
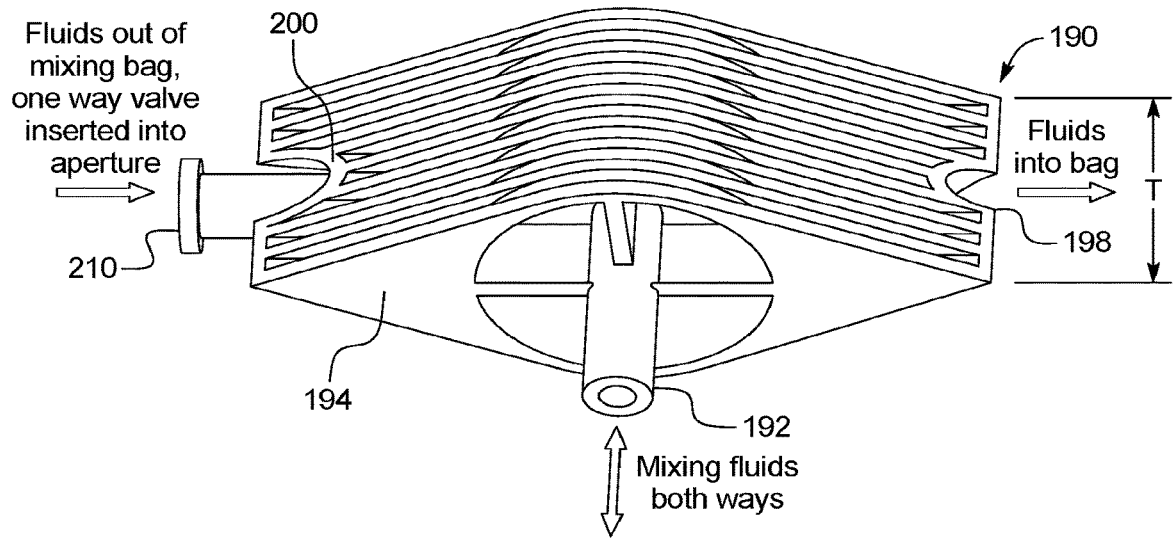
FIGS. 5A and 5B are different perspective views of one embodiment of a connector used with the second primary heater/mixing container or bag of the present disclosure.
Figure 5B:
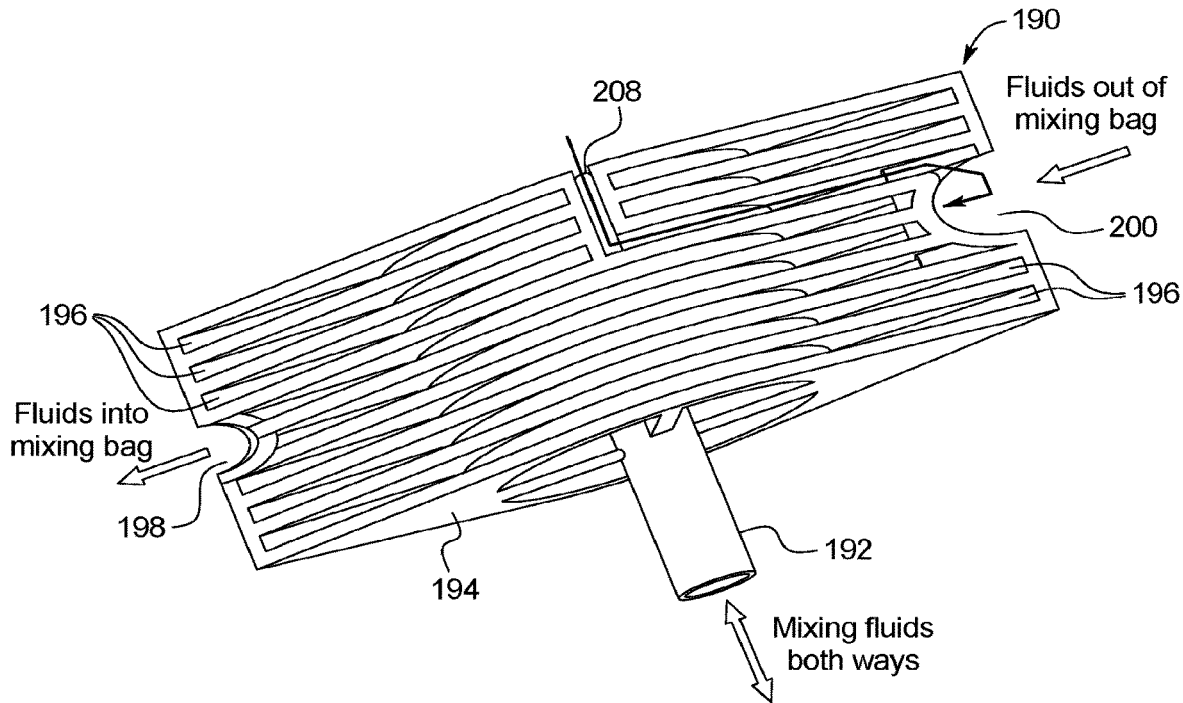

Referring now to FIGS. 4, 5A and 5B, in a second primary embodiment, container or bag 160*b* may again include a first, proximal end 162, a second, distal end 164 and a pair of opposing sides 166*a* and 166*b* extending between the first and second ends. Container or bag 160*b* may be square or rectangular or have one or more curved end or surface. FIG. 4 illustrates that container 160*b* is in one embodiment a flexible bag formed via sheets 180*a*, 180*b* made of any of the materials disclosed herein.

FIGS. 4, 5A and 5B illustrate that an alternative connector 190 is placed in sealed communication with sheets 180*a*, 180*b* at first end 162 of container or bag 160*b*. For example, sheets 180*a*, 180*b* at first end 162 of flexible bag 160*b* may be heat sealed, sonically or ultrasonically sealed, solvent bonded and/or adhered to connector 190, which may be a rigid or semi-rigid plastic made of any of the materials disclosed herein. Connector 190 in the second primary embodiment does not Y or T together outside of the container or bag, and instead includes a single port 192 sealed to the heater/mixing line extending to the cassette. Single port 192 may be formed integrally as part of a same mold with the rest of connector 190 and be connected via a luer connection to heater/mixing line 60, or be connected via a compression fitting, e.g., barbed fitting, to heater/mixing line 60.

Connector 190 of the second primary embodiment in the illustrated embodiment includes a tapered body 194, wherein the body has a thickness T (FIG. 5A) that enables multiple grooves 196 e formed on the upper and lower surfaces of the tapered body 194. The tapering of body 192 helps create a strong seal with flexible sheets 180*a* and 180*b*. Tapered body 194 also defines an inlet aperture 198 for allowing the WFPD and at least one concentrate to enter container 160*b* from cassette 42 and an outlet aperture 200 for allowing mixed or further mixed WFPD and at least one concentrate to exit container 160 towards cassette 42. Inlet aperture 198 and outlet aperture 200 are both in fluid communication with port 192, e.g., via a T connection located within tapered body 194.

In the illustrated embodiment, the inlet aperture 198 of connector 160*b* is placed in fluid communication with an inlet passageway 202 (FIG. 4) defined in the illustrated embodiment by the container itself, e.g., a passageway formed via seals made between flexible sheets 180*a* and 180*b* forming bag or container 160*b*. FIG. 4 illustrates an interior welded, bonded, adhered or otherwise sealed seam 204 that in combination with a seam creating side 166*b* forms passageway 202.

Inlet passageway 202, like the inlet leg tube 176 of the first primary embodiment, may extend to the second or distal end 164 of container 160*b*, e.g., to a corner of the second or distal end 164 of container 160*b* diagonally opposite from a corner at the first or proximal end of the container at which connector 190 is located. The distal end 206 of inlet passageway 202 is open to the interior of container or bag 160*b*. In this manner, the WFPD and at least one concentrate may be introduced into the interior of container 160*b* at its second or distal end 164 and be removed from the container at its first or proximal end 162.

As illustrated in FIGS. 5A and 5B, outlet aperture 200 of connector 190 is in one embodiment placed in fluid communication with the plurality of grooves 196 formed along the upper and lower surfaces of the connector. Connector 190 is sealed to the remainder of the container, e.g., to flexible sheets 180*a* and 180*b*, such that the further mixed WFPD and at least one concentrate can enter grooves 196 from at least one entry location 208 (FIG. 5B) and flow through grooves 196 to outlet aperture 200, and from the outlet aperture out of container or bag 160*b* and through heater/mixing line 60 to cassette 42. Sealed grooves 196 are formed between flexible sheets 180*a* and 180*b* and body 194, enabling the further mixed WFPD and at least one concentrate to be funneled from the at least one entry location 208 to outlet aperture 200.

As illustrated in FIG. 5A, in one embodiment a one way valve 210, such as a duckbilled check valve, is placed into, or adjacent to, outlet aperture 200, so that when heater/mixing line 60 is placed under positive pressure to drive the WFPD and at least one concentrate into container or bag 160*b*, the WFPD and at least one concentrate are prevented from flowing from the inside of the container, through grooves 196 of connector 190 and out of the connector into heater/mixing line 60. It is believed that a second one way valve is not needed for inlet aperture 198 of connector 190 because when heater/mixing line 60 is placed under negative pressure to pull the further mixed WFPD and at least one concentrate from container or bag 160*b*, flexible passageway 202, made by sealing together bag sheets 180*a* and 180*b* in one embodiment to create seams defining the passageway, collapses under the negative pressure, causing inlet passageway 198 to close itself and preventing the WFPD and at least one concentrate from being pulled out of container 160*b* via the inlet passageway before the WFPD and at least one concentrate have a chance to mix in the container.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
   a source of water made suitable for a dialysis treatment;
   at least one concentrate for mixing with the water from the source;
   a dialysis fluid pump; and
   a disposable set operable with the dialysis fluid pump and in fluid communication with the source of water and the at least one concentrate, the disposable set including a container having a first proximal end and a second distal end, the container configured such that the water and the at least one concentrate pumped by the dialysis fluid pump enters at the second distal end and exits from the first proximal end, via a passageway extending from the first proximal end to the second distal end, to mix for the dialysis treatment,
   wherein the first proximal end includes a connector, the connector defining at least one groove positioned and arranged on an outer surface of the connector,
   the at least one groove is configured to allow the water and the at least one concentrate, which are at least partially mixed together, to travel through the at least one groove formed between the connector and the container to a port of the container, and
   the connector is associated with at least one one-way valve configured to prevent the water and the at least one concentrate from flowing from an inside of the container and back through the passageway towards the first proximal end.

2. The dialysis system of claim 1, which is configured such that the water and the at least one concentrate pumped by the dialysis fluid pump enter the container partially mixed together.

3. The dialysis system of claim 1, wherein the container is a flexible bag formed from flexible sheets, and wherein the flexible sheets include a first flexible sheet and a second flexible sheet.

4. The dialysis system of claim 1, wherein the disposable set includes a pumping cassette that interfaces with the dialysis fluid pump.

5. The dialysis system of claim 4, wherein the water and the at least one concentrate are mixed initially in the pumping cassette.

6. The dialysis system of claim 4, wherein the dialysis fluid pump pneumatically actuates the pumping cassette.

7. The dialysis system of claim 4, wherein the disposable set includes a tube extending from the pumping cassette to the container.

8. The dialysis system of claim 7, wherein the tube is a first tube and wherein the disposable set includes at least one second tube extending from the pumping cassette to the at least one concentrate.

9. The dialysis system of claim 7, wherein the tube is a first tube and wherein the disposable set includes a second tube extending from the pumping cassette to an accumulator that receives the water made suitable for the dialysis treatment from the source.

10. The dialysis system of claim 4, which is configured to pump the water and the at least one concentrate back and forth from the pumping cassette to the container a plurality of times to perform a mixing sequence for further mixing.

11. The dialysis system of claim 1, wherein the passageway is a tube extending within the container from the port to the second distal end of the container.

12. The dialysis system of claim 11, which is configured to deliver the water and the at least one concentrate into the container via the tube at the second distal end and remove further mixed water and at least one concentrate from the container via the connector at the first proximal end.

13. The dialysis system of claim 1, wherein the container is sealed so as to form a passageway leading to the second distal end of the container.

14. The dialysis system of claim 1, wherein the port is formed as part of the connector.

15. The dialysis system of claim 1, wherein the container is sealed so as to form the passageway leading to the second distal end of the container, and wherein the passageway extends from and fluidly communicates with an aperture defined by the connector.

16. The dialysis system of claim 15, wherein the aperture is a first aperture and which includes a second aperture defined by the connector, the second aperture allowing the water and the at least one concentrate at least partially mixed for the dialysis treatment to exit the container.

17. The dialysis system of claim 16, wherein the at least one one-way valve is a first one-way valve, and wherein the second aperture is fitted with or located adjacent to the first one-way valve.

18. The dialysis system of claim 13, wherein the passageway is structured to collapse under negative pressure.

19. A dialysis system comprising:
a source of water made suitable for a dialysis treatment;
at least one concentrate for mixing with the water from the source; and
a disposable set in fluid communication with the source of water and the at least one concentrate, the disposable set including a container having a first proximal end and a second distal end, the container including (i) a tube structured and arranged within the container, the tube extending from the first proximal end to the second distal end such that the water and the at least one concentrate to flow through the tube and enter the container at the second distal end and (ii) a port at the first proximal end, the port associated with at least one one-way valve such that the water and the at least one concentrate at least partially mixed for the dialysis treatment exit the first proximal end of container while the at least one one-way valve prevents the water and the at least one concentrate from traveling back through the tube towards the first proximal end, wherein the first proximal end of the container includes a connector, the port forming part of the connector, and wherein the connector is placed in fluid communication with the tube.

20. The dialysis system of claim 19, wherein the tube and the port connect at a junction outside of the container.

21. The dialysis system of claim 19, wherein the at least one one-way valve is a first one-way valve, and wherein at least one of the tube and the port is fitted with the first one-way valve.

22. A dialysis system comprising:
a source of water made suitable for a dialysis treatment;
at least one concentrate for mixing with the water from the source; and
a disposable set in fluid communication with the source of water and the at least one concentrate, the disposable set including a container having at least one outer seal forming a first proximal end and a second distal end, the container sealed within the at least one outer seal so as to form a passageway leading to the second distal end of the container, the container further including a port at the first proximal end, the port associated with at least one one-way valve, wherein
the passageway is structured and arranged such that the water and the at least one concentrate enter the passageway, from the port at the first proximal end, and flow, according to the at least one one-way valve, through the passageway to enter the container at the second distal end, and
the port is structured and arranged such that the water and the at least one concentrate that have at least partially mixed for the dialysis treatment to exit the first proximal end of the container while the at least one one-way valve prevents the water and the at least one concentrate from traveling back through the passageway.

23. The dialysis system of claim 22, wherein the first end of the container includes a connector, the connector defining at least one groove positioned and arranged to allow the water and the at least one concentrate that have at least partially mixed within the container for dialysis treatment to travel through the at least one groove to the port to exit the container.

24. The dialysis system of claim 23, wherein the port is formed as part of the connector.

25. The dialysis system of claim 24, wherein the passageway extends from and fluidly communicates with an aperture defined by the connector.

26. The dialysis system of claim 25, wherein the aperture is a first aperture and which includes a second aperture defined by the connector, the second aperture allowing the water and the at least one concentrate at least partially mixed for the dialysis treatment to exit the container.

27. The dialysis system of claim 26, wherein the at least one one-way valve is a first one-way valve, and wherein the second aperture is fitted with or adjacent to the first one-way valve.

28. The dialysis system of claim 22, wherein the passageway is structured to collapse under negative pressure.

* * * * *